US00PP13037P2

(12) United States Plant Patent
Noodelijk

(10) Patent No.: US PP13,037 P2
(45) Date of Patent: Oct. 1, 2002

(54) CHRYSANTHEMUM PLANT NAMED 'APOLLORES'

(75) Inventor: Robert Noodelijk, Woubrugge (NL)

(73) Assignee: Chrysanthemum Breeders Association, N.V. (NL)

( * ) Notice: Subject to any disclaimer, the term of this patent is extended or adjusted under 35 U.S.C. 154(b) by 0 days.

(21) Appl. No.: 09/734,655

(22) Filed: Dec. 13, 2000

(51) Int. Cl.[7] ..... A01H 5/00
(52) U.S. Cl. ..... Plt./289
(58) Field of Search ..... Plt./289

(56) References Cited

PUBLICATIONS

UPOV–ROM GTITM Computer Database 2000/04 GTI JOUVE Retrieval Software, citation(s) for Apollo Aug. 6, 2001.*

* cited by examiner

*Primary Examiner*—Bruce R. Campell
*Assistant Examiner*—Annette H. Para
(74) *Attorney, Agent, or Firm*—Parkhurst & Wendel, L.L.P.

(57) ABSTRACT

A chrysanthemum plant named 'Apollores' characterized by its small sized blooms with yellow ray florets and prolific branching; natural season flower date September 11–17; blooming for a period of 5 weeks.

3 Drawing Sheets

BACKGROUND OF THE INVENTION

'Appollores' is a product of a breeding and selection program for outdoor pot mums (garden mums) which had the objective of creating new chrysanthemum cultivars with a decorative type flower, a natural season flower date around September 11–17; blooming for a period of 5 weeks. The new plant of the present invention comprises a new and distinct cultivar of Chrysanthemum plant 'Apollores' is a seedling resulting from the open pollination among groups of chrysanthemum cultivars maintained under the control of the inventor for breeding purposes. The new and distinct cultivar was discovered and selected as one flowering plant by Rob Noodelijk on a cultivated field in Rijsenhout Holland in September 1998. The plant has been asexually reproduced by cuttings in greenhouses at Rijsenhout Holland. The new cultivar has been found to retain its distinctive characteristics through successive propagations.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
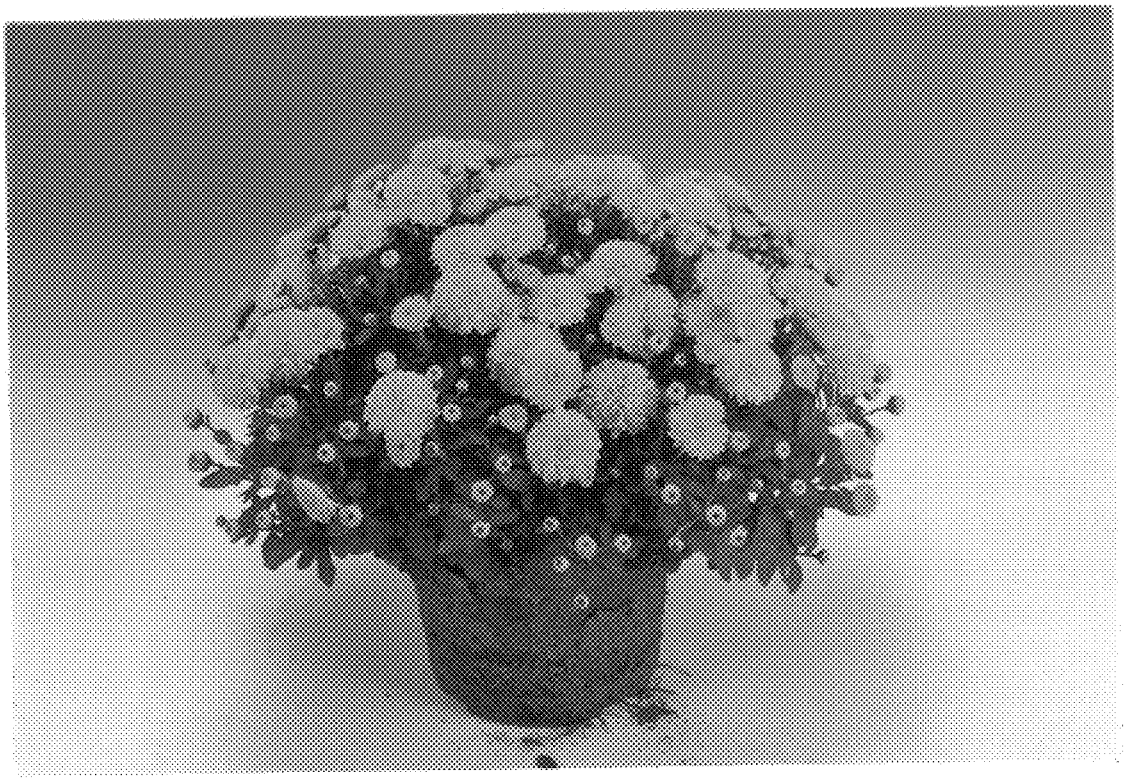
FIG. 1 shows a plant of the cultivar in full bloom.
Figure 2:
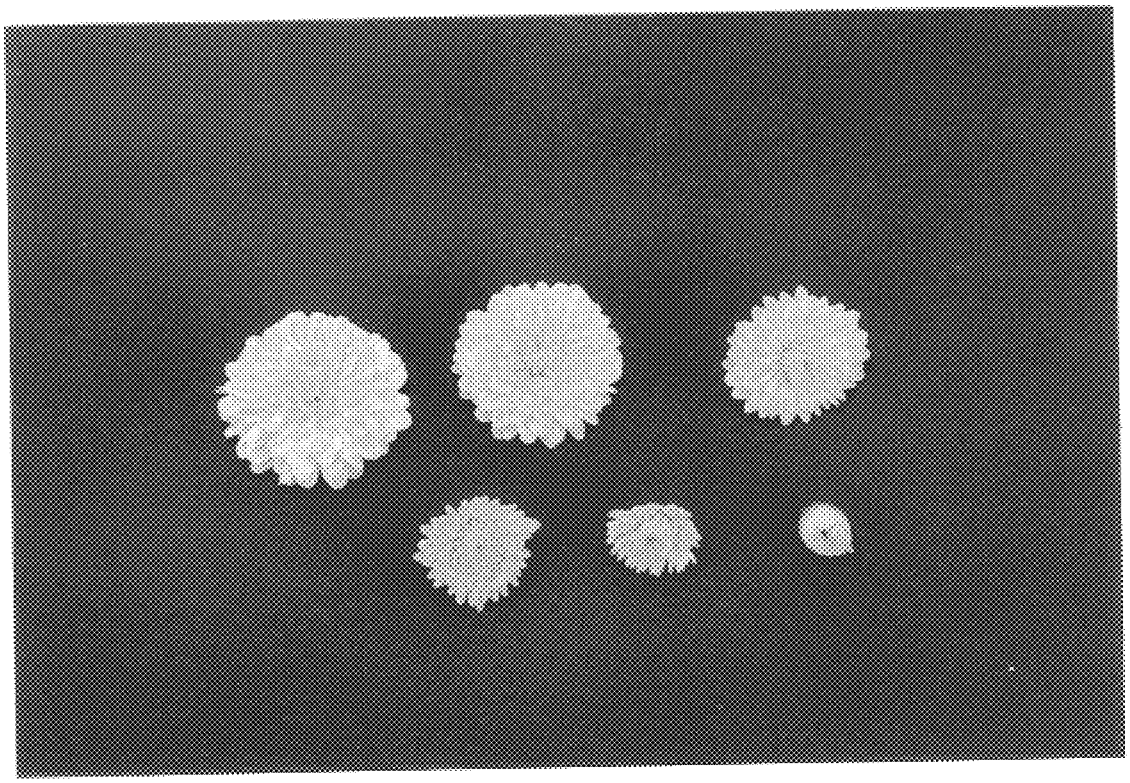
FIG. 2 shows the various stages of bloom of the new cultivar.
Figure 3:
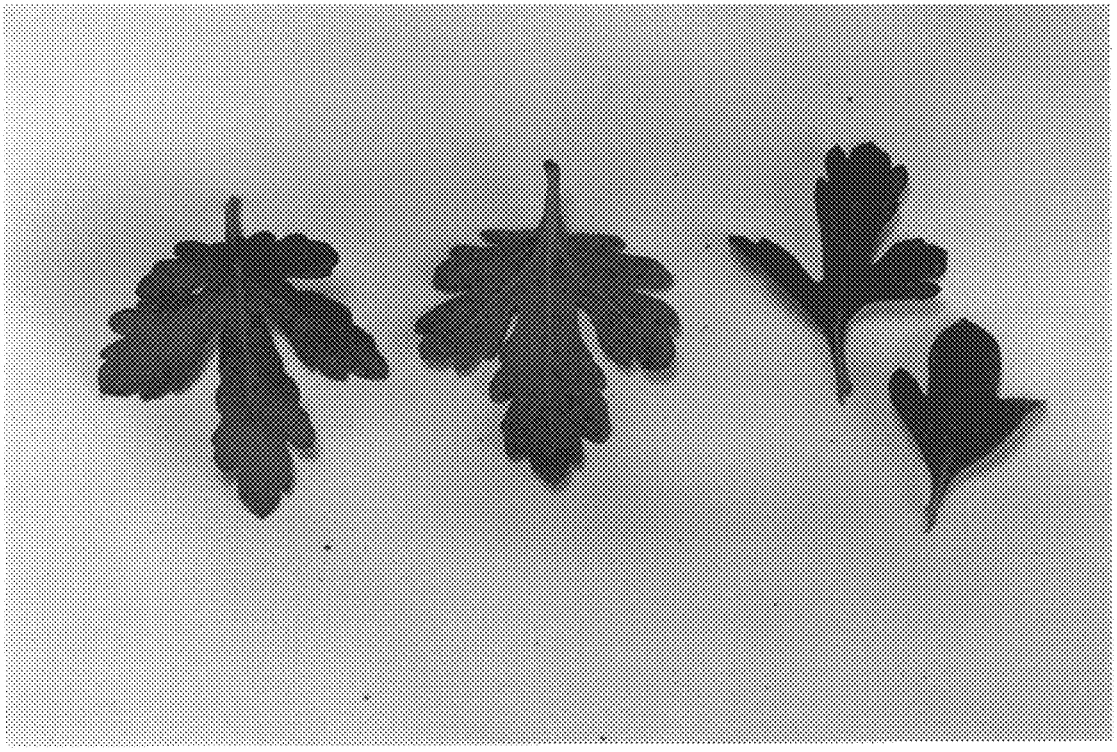
FIG. 3 shows the various stages of foliage and petiole of the new cultivar.

This new variety of chrysanthemum is of the botanical classification *dendranthema grandiflora*. The observations and measurements were gathered from plants grown out door in Rijsenhout, Holland under natural day length and temperature and planted week 22 in 1999 and 2000. The natural blooming date of this crop was September 11–17 (week 37). The age of the observed plant is 15 weeks. The average height of the plants was 30–35 cm cms. No growth retardants were used. No tests were done on disease or insects resistance or susceptibility. No tests were done on cold or drought resistance. This new variety produces small sized blooms with yellow ray florets and a reddish/yellow center blooming for a period of 5 weeks.

From the cultivars known to inventor the most similar existing cultivar in comparison to 'Apollo' is 'YELLOW NICOLE' (U.S. Plant Pat. No. 8,757). When 'YELLOW NICOLE' (U.S. Plant Pat. No. 8,757) and 'Apollores' are being compared the following differences are noticed: The differences of 'YELLOW NICOLE' (U.S. Plant Pat. No. 8,757) and 'Apollores' are (1) Natural blooming date and (2) flower color.

The following is a description of the plant and characteristics that distinguish 'Apollores' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 1995.

Table 1: Botanical Description of CULTIVAR 'Apollores'

Bud:
- *Size*.—Small; cross-section 1.0 cm, height 0.9 cm.
- *Outside color*.—Yellow 9A.
- *Involucral bracts*.—2 rows, length 7 mm, width 3 mm.
- *Involucral bracts among disc-florets*.—Not present.
- *Involucral bracts color*.—Green 138 B.

Bloom:
- *Type*.—Decorative.
- *Height*.—High, 3.0–3.5 cm.
- *Size*.—Small.
- *Fully expanded*.—4.0–4.5 cm.
- *Number of blooms per branch*.—Approx. 4–6 blooms per branch.
- *Performance on the plant*.—5 weeks.
- *Seeds*.—Not produced.
- *Fragrance*.—Typical chrysanthemum.

Color:

*Center of the flower* (*a section of the ray*).—Immature yellow 9 A, tipped greyed—orange 168 A, Mature yellow 12 A.

*Color of upper surface of the ray-florets*.—Yellow 9 A.

*Color of the lower surface of the ray-florets*.—Yellow 6 C.

*Tonality from distance*.—A garden mum with yellow flowers.

*Discoloration to color*.—Yellow 7 A.

Ray florets:

*Texture*.—Upper and under side smooth.

*Number*.—160–180.

*Cross-section*.—Concave sometimes flat.

*Longitudinal axis of majority of the ray-florets*.—Straight sometimes incurved.

*Length of corolla tube*.—Medium, 0.8–1.0 cm.

*Ray-floret margin*.—Entire.

*Ray-floret length*.—2.0–2.2 cm.

*Ray-floret width*.—0.4–0.7 cm.

*Ratio length/width*.—Medium.

*Shape of tip*.—Rounded.

*Disc florets*.—Not present.

*Receptacle shape*.—Domed raised.

Reproductive organs:

*Stamen*.—Not present.

*Pollen*.—Not present.

*Styles*.—Thin.

*Style color*.—Yellow-green.

*Style length*.—4 mm.

*Stigmas color*.—Yellow-green.

*Stigma width*.—1 mm.

*Ovaries*.—Enclosed in calyx.

Plant:

*Shape*.—Rounded sometimes flat.

*Growth habit*.—Spreading.

*Growth rate*.—Moderate.

*Height*.—30–35 cm.

*Width*.—29–33 cm.

*Stem color*.—Green 138 B.

*Stem strength*.—Strong.

*Stem brittleness*.—Present.

*Stem anthocyanin coloration*.—Absent.

*Length of lateral branch*.—From top to bottom 12–14 cm.

*Lateral branch color*.—Green 138 B.

*Lateral branch, attachment*.—Strong.

*Branching* (*average number of lateral branches*).—Prolific with 5–7 breaks after pinching.

*Peduncle length*.—4.0–4.5 cm.

*Peduncle color*.—Green 138 B.

*Natural season blooming date*.—September 11–17.

Foliage:

*Color*.—Upper side green 147 B. Under side green 147 C.

*Size*.—Small; length 6.5 cm, width 5.5 cm.

*Quantity* (*number per lateral branch*).—10–12.

*Shape*.—Rounded.

*Texture upper side*.—Glabrous.

*Texture under side*.—Pubescent.

*Venation arrangement*.—Palmate.

*Shape of the margin*.—Serrated.

*Shape of base of sinus between lateral lobes*.—Acute.

*Margin of sinus between lateral lobes*.—Converging.

*Shape of base*.—Attenuate.

*Apex*.—Mucronate.

TABLE 2

Differences with the comparison varieties

| | 'Apollores' | 'Yellow Nicole' |
|---|---|---|
| Natural blooming date | 11–17 September | 22–26 September |
| Flower color | Yellow 9 A | Yellow 5 A |
| Flower color of center when immature | Yellow 9 A tipped greyed-orange 168 A | Yellow 7 A |

I claim:

1. A new and distinct variety of chrysanthemum plant as described and illustrated.

* * * * *